United States Patent [19]

Rosini et al.

[11] Patent Number: 5,362,750
[45] Date of Patent: Nov. 8, 1994

[54] 4,5-DIHYDROXY- AND 4,5,8-TRIHYDROXY-9,10-DIHYDRO-9,10-DIOXO-2-ANTHRACENECARBOXYLIC ACID DICARBONATES AND URETHANS HAVING THERAPEUTICAL ACTIVITIES

[75] Inventors: Sergio Rosini; Maurizio Mian, both of Pisa, Italy

[73] Assignee: Istituto Gentili S.p.A., Pisa, Italy

[21] Appl. No.: 70,382

[22] PCT Filed: Dec. 3, 1991

[86] PCT No.: PCT/EO91/02290
§ 371 Date: Jun. 7, 1993
§ 102(e) Date: Jun. 7, 1993

[87] PCT Pub. No.: WO92/10464
PCT Pub. Date: Jun. 25, 1992

[30] Foreign Application Priority Data

Dec. 11, 1990 [IT] Italy ................... 22343 A/90

[51] Int. Cl.$^5$ ............... A01N 37/00; A61K 31/21; C07C 271/44; C07C 323/12
[52] U.S. Cl. ........................ 514/510; 552/262
[58] Field of Search ................. 552/262; 514/510

[56] References Cited

U.S. PATENT DOCUMENTS 5,030,387 7/1991 Matsuoka et al. ............... 552/262

OTHER PUBLICATIONS

March Advanced Organic Chemistry, Wiley & Sons, N.Y., 1985, p. 347.

Primary Examiner—Johann Richter
Assistant Examiner—Rebecca Cook
Attorney, Agent, or Firm—Bucknam and Archer

[57] ABSTRACT 4,5-Dihydroxy- and 4,5,8-trihydroxy-9,10-dihydro-9,10-dioxo-2-anthracenecarboxylic acid dicarbonates and urethanes having therapeutic activities, a process for the preparation thereof and pharmaceutical compositions containing them.

8 Claims, No Drawings

4,5-DIHYDROXY- AND 4,5,8-TRIHYDROXY-9,10-DIHYDRO-9,10-DIOXO-2-ANTHRACENECARBOXYLIC ACID DICARBONATES AND URETHANS HAVING THERAPEUTICAL ACTIVITIES

The present invention relates to 2-anthracenecarboxylic derivatives of general formula (I)

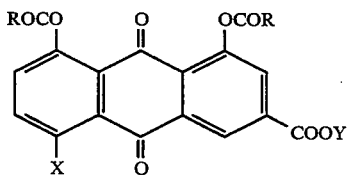

wherein:
X is hydrogen or a OCOR group, in which R is as defined below;
Y is hydrogen, $C_1$-$C_{20}$ alkyl; $C_1$-$C_{16}$ alkoxyethyl; $C_1$-$C_{16}$ alkylthioethyl;
R is a straight, branched or cyclic $C_1$-$C_{20}$ alkoxy, aryloxy, benzyloxy, 2-phenylethoxy group; $R^1R^2N$, wherein $R^1$ and $R^2$ which can be the same or different, are selected from hydrogen; straight, branched or alicyclic $C_1$-$C_{10}$ alkyl, phenyl, benzyl, 2-phenylethyl; and to the pharmaceutically acceptable salts thereof.

Preferred compounds of the invention are those in which R is selected from: methoxy, ethoxy, propoxy, butoxy, benzyloxy, methylamino, ethylamino, propylamino, benzylamino; Y is hydrogen or $C_1$-$C_4$ alkyl, ethoxyethyl or ethylthioethyl.

Exemplifications of pharmaceutically acceptable salts are the salts with alkali or alkaline-earth metals, such as sodium, potassium, calcium or magnesium salts; and the salts with organic bases, such as ethanolamine, diethanolamine, N,N-dialkylethanolamine, phenylethylamine, piperazine, morpholine, lysine and the like.

Compounds having a 9,10-anthraquinone structure, such as diacetylrhein, are known to have antiarthritic activity (DE 2711493).

Italian Patent application n. 21456 A/87 discloses rhein derivatives wherein the hydroxy groups are replaced by thio groups.

Now it has been found that rhein and 8-hydroxyrhein carbonic esters and urethans, of formula (I), have a marked inhibitory activity against the enzymes involved in articular pathology. Particularly, the compounds of the invention proved to have a surprising effect on mammal collagenase and elastase activities, thus being advantageous in the therapeutical treatment of arthritic conditions.

Said activities are particularly important in the treatment of cartilage pathology as well as in that of collagenous tissues.

Among the observed activities, particularly important are the inhibition of free radical formation and the inhibition of spontaneous auto-lysis of cartilages.

The compounds of the invention in which R is different from $NR^1R^2$ are prepared by reacting one compound of formula (II)

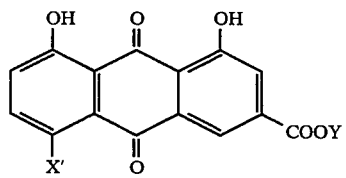

wherein X' is hydrogen or OH and Y is as defined above, with a chlorocarbonate of formula (III)

ROCOCl      (III)

wherein R is as defined above.

Compounds (II) wherein Y is an alkyl, alkoxyethyl or alkylthioethyl group can be prepared by means of conventional esterification methods of compounds (II) in which Y is hydrogen.

Compounds (I) in which R is a $NR^1R^2$ group are prepared by reacting a compound of formula (II) above with phosgene and subsequently with a compound of formula

wherein $R^1$ and $R^2$ are as defined above.

Alternatively, compounds (I) wherein R is $NR^1R^2$ are prepared by reacting a compound of formula (II) with a compound of formula $R^1R^2NOCl$, wherein $R^1$ and $R^2$ are as defined above.

The compounds of the invention can be used as such or in form of pharmaceutically acceptable salts thereof, in the preparation of medicaments, together with suitable conventional carriers.

Examples of solid formulations are tablets, capsules, pills, or other forms of suitable bio-availability. Dosages can range from 5 to 500 mg per unit dose, the daily dose depending on the severity of the arthritic pathology and the patient's conditions, according to the physician judgement.

The following Examples further illustrate the invention.

EXAMPLE 1

Preparation of 4,5-bis(methoxycarbonyloxy)-9,10-dihydro-9,10-dioxo-2-anthracenecarboxylic 2.84 g (0.01 mole) of acid (I) in 50 ml of anhydrous tetrahydrofuran are placed into a two-necked flask fitted with a thermometer and a dropper with $CaCl_2$ valve, then 3.03 g (0.03 mole) of anhydrous triethylamine are added. 2.08 g (0.022 mole) of methyl chloroformate dissolved in 5-10 ml of anhydrous tetrahydrofuran are dropped into the stirred mixture, at 5° C. The reaction temperature must be kept below 30° C. When dropping is over (after about 4 hours) the precipitate is filtered, the solvent is evaporated off under vacuum from the filtrate and the fluid residue is treated with water and acidified with diluted HCl to pH 3–4. The product precipitates and it is dried.

| Elementary analysis for $C_{19}H_{12}O_{10}$ | | |
|---|---|---|
| | theoretical % | found % |
| C | 57,00 | 56,94 |

-continued

| Elementary analysis for $C_{19}H_{12}O_{10}$ | | |
|---|---|---|
| | theoretical % | found % |
| H | 3,02 | 2,98 |
| O | 39,97 | 39,87 |

IR in conformity.

EXAMPLES 2-7

Following the procedure described in Example 1, the following compounds are obtained:

| Ex. n. | X | R | Y | Formula |
|---|---|---|---|---|
| 2 | H | $C_2H_5O$ | H | $C_{21}H_{16}O_{10}$ |
| 3 | H | $C_3H_7O$ | H | $C_{23}H_{20}O_{10}$ |
| 4 | H | $C_4H_9O$ | H | $C_{25}H_{24}O_{10}$ |
| 5 | H | $C_7H_7O$ | H | $C_{31}H_{20}O_{10}$ |
| 6 | OCOR | $CH_3O$ | H | $C_{21}H_{14}O_{13}$ |
| 7 | OCOR | $C_2H_5O$ | H | $C_{24}H_{20}O_{13}$ |

The spectroscopical and elementary analysis data confirm the proposed structures.

EXAMPLE 8

Preparation of 4,5,8-tris(methylaminocarbonyloxy)-9,10-dihydro-9,10-dioxo-2-anthracenecarboxylic acid 2.84 g of acid (I) are suspended in 70 ml of anhydrous tetrahydrofuran. The suspension is cooled to 0° C., it is added with 3.03 g (0.03 mole) of anhydrous triethylamine, then 16 ml of a solution of 20% phosgene in toluene are dropped therein. The reaction proceeds for 24 hours, always keeping temperature at about 0° C. After that, solvent is evaporated off under vacuum and the obtained bis-chloroformate is directly used to prepare the urethan. (Chloroformate formation can be monitored by T.L.C., using 9:1 tetrahydrofuran/water as the eluent. A small amount of chloroformate is treated with a t-butylamine excess, then the excess is removed under vacuum and the residue is dissolved in methanol. The chromatographic plate can directly be seeded with such a solution).

The obtained bis-chloroformate is freed from the solvent and suspended in 40 ml of anhydrous tetrahydrofuran at 0° C. 1.55 g (0.05 mole) of methylamine are dropped into the suspension, keeping temperature at 0° C. The reaction is immediate. The suspension is filtered, the filtrate is evaporated under vacuum and the residue is washed with distilled water. The precipitate is filtered, dried and suitably crystallized.

| Elementary analysis for $C_{19}H_{14}N_2O_8$ | | |
|---|---|---|
| | theoretical % | found % |
| C | 57,29 | 57,36 |
| H | 3,54 | 3,52 |
| N | 7,02 | 7,10 |

IR in conformity.

EXAMPLES 9-12

Following the procedure described in Example 8, starting from the appropriate reagents, the following compounds are obtained:

| ES. N. | X | Y | R | Formula |
|---|---|---|---|---|
| 9 | H | H | $C_2H_5NH$ | $C_{21}H_{18}N_2O_8$ |
| 10 | H | H | $C_3H_7NH$ | $C_{23}H_{22}N_2O_8$ |
| 11 | H | H | $C_4H_9NH$ | $C_{25}H_{26}N_2O_8$ |
| 12 | H | H | $C_7H_7NH$ | $C_{31}H_{22}N_2O_8$ |

The spectroscopical and elementary analysis data confirm the proposed structures.

The compounds of Examples 8 and 9 can also be prepared from the corresponding chloroamides, which react with acid (I).

The procedure is as follows:

2.84 g (0.01 mole) of acid (I) are suspended in 70 ml of tetrahydrofuran. The suspension is cooled to 0° C. and added with 3.03 g (0.03 mole) of anhydrous triethylamine and 0.02 mole of N,N-dialkylchloroamide. The urethan immediately forms, together with a precipitate which is filtered off. The clear solution is evaporated under reduced pressure to obtain a residue which is suitably crystallized.

EXAMPLES 13-14

Following the procedure described in Example 8, starting from the appropriate reagents, the following products are obtained:

| ES. N. | X | Y | R | Formula |
|---|---|---|---|---|
| 13 | H | H | $CH_3NH$ | $C_{21}H_{17}N_3O_{10}$ |
| 14 | OCOR | H | $C_2H_5NH$ | $C_{24}H_{23}N_3O_{10}$ |

The spectroscopical and elementary analysis data confirm the proposed structures.

EXAMPLE 15

Preparation of 4,5-dihydroxy-9,10-dihydro-9,10-dioxo-2-anthracenecarboxylic acid butyl ester 7.4 g (0.02 mole) of 4,5-bis(acetoxy)-9,10-dihydro-9,10-dioxo-2-anthracenecarboxylic acid are dissolved in 150 ml of butanol. Gaseous HCl is bubbled through the obtained solution until saturation. The reaction mixture is left to react for half an hour at room temperature, then it is heated to 60°-70° C. for 3 hours, while continuing HCl bubbling. The desired product precipitates, which is cooled, filtered and crystallized from ethyl acetate.

| Elementary analysis for $C_{19}H_{16}O_6$ | | |
|---|---|---|
| | theoretical % | found % |
| C | 67,05 | 67,00 |
| H | 4,73 | 4,70 |
| O | 28,20 | 28,27 |

IR in conformity.

EXAMPLES 16-17

Following the procedure described in Example 15, starting from the appropriate reagents, the following compounds are obtained:

| ES. N. | X | Y | R | Formula |
|---|---|---|---|---|
| 16 | OH | $C_4H_9$ | H | $C_{21}H_{18}O_8$ |

-continued

| ES. N. | X | Y | R | Formula |
|---|---|---|---|---|
| 17 | H | $C_2H_5OC_2H_5$ | H | $C_{19}H_{16}O_7$ |

The spectroscopical and elementary analysis data confirm the proposed structures.

EXAMPLE 18

Preparation of 4,5-dihydroxy-9,10-dihydro-9,10-dioxo-2-anthracenecarboxylic acid ethylthioethyl ester 7.4 g (0.02 mole) of 4,5-bis(acetyloxy)-9,10-dihydro-9,10-dioxo-2-anthracenecarboxylic acid are dissolved in 40 ml of $SOCl_2$. The reaction mixture is left to react for 2 hours under stirring, then the thionyl chloride excess is evaporated off under vacuum, the residue is washed with anhydrous benzene and solvent is evaporated off under vacuum. The formed chloride is dissolved in 200 ml of chloroform and the obtained solution is dropped into a mixture of 2 g (0.02 mole) of triethylamine and 2.2 g (0.02 mole) of 2-ethyl-thioethyl alcohol in 40 ml of chloroform, at a temperature of 0°–10° C. The reaction is almost immediate at room temperature. After that, solvent is evaporated off under vacuum, the residue is taken up into 40 ml of benzene and filtered. The filtrate is treated with 10% $NH_3$ and it is left to react for about 12 hours at room temperature. The solution is acidified to pH 5–6 with diluted HCl. A precipitate is obtained which can be filtered, containing the crude product. The crude product is washed with acetone, filtered and purified by silica gel chromatography, using ethyl acetate as the eluent.

| Elementary analysis for $C_{19}H_{16}O_6S$ | | |
|---|---|---|
|  | theoretical % | found % |
| C | 61,28 | 61,33 |
| H | 4,33 | 4,31 |
| O | 8,59 | 8,64 |

IR in conformity.

EXAMPLE 19

Preparation of 4,5-bis(methoxycarbonyloxy)-9,10-dihydro-9,10-dioxo-2-anthracenecarboxylic acid butyl ester 2.7 g (8 mmoles) of the product of Example 15 are dissolved in 100 ml of anhydrous tetrahydrofuran; the resulting solution is added first with 2.42 g (24 mmoles) of anhydrous triethylamine, then, after cooling to 0°–5° C., with 1.6 g (17 mmoles) of methyl chloroformate. The reaction is complete within 3 hours, keeping room temperature. After that, solvent is evaporated off under reduced pressure and the residue is washed with acidulated water, the product is filtered, washed and crystallized from ethyl ether. M.p. 200°–202° C.

| Elementary analysis for $C_{23}H_{20}O_{10}$ | | |
|---|---|---|
|  | theoretical % | found % |
| C | 60,52 | 60,47 |
| H | 4,41 | 4,39 |
| O | 35,05 | 35,00 |

IR in conformity.

EXAMPLES 20–35

Following the procedure described in Example 19, starting from the appropriate reagents, the following compounds are obtained:

| ES. N | X | Y | R | Formula |
|---|---|---|---|---|
| 20 | H | $C_4H_9$ | $C_2H_5O$ | $C_{25}H_{24}O_{10}$ |
| 21 | H | $C_4H_9$ | $C_3H_7O$ | $C_{27}H_{28}O_{10}$ |
| 22 | H | $C_4H_9$ | $C_4H_9O$ | $C_{29}H_{32}O_{10}$ |
| 23 | H | $C_4H_9$ | $C_7H_7O$ | $C_{35}H_{28}O_{10}$ |
| 24 | OCOR | $C_4H_9$ | $CH_3O$ | $C_{25}H_{22}O_{13}$ |
| 25 | OCOR | $C_4H_9$ | $C_2H_5O$ | $C_{28}H_{28}O_{13}$ |
| 26 | H | $C_2H_5OC_2H_5$ | $CH_3O$ | $C_{23}H_{20}O_{11}$ |
| 27 | H | $C_2H_5OC_2H_5$ | $C_2H_5O$ | $C_{25}H_{24}O_{11}$ |
| 28 | H | $C_2H_5OC_2H_5$ | $C_3H_7O$ | $C_{27}H_{28}O_{11}$ |
| 29 | H | $C_2H_5OC_2H_5$ | $C_4H_9O$ | $C_{29}H_{32}O_{11}$ |
| 30 | H | $C_2H_5OC_2H_5$ | $C_7H_7O$ | $C_{35}H_{28}O_{11}$ |
| 31 | H | $C_2H_5SC_2H_5$ | $CH_3O$ | $C_{23}H_{20}O_{10}S$ |
| 32 | H | $C_2H_5SC_2H_5$ | $C_2H_5O$ | $C_{25}H_{24}O_{10}S$ |
| 33 | H | $C_2H_5SC_2H_5$ | $C_3H_7O$ | $C_{27}H_{28}O_{10}S$ |
| 34 | H | $C_2H_5SC_2H_5$ | $C_4H_9O$ | $C_{29}H_{32}O_{10}S$ |
| 35 | H | $C_2H_5SC_2H_5$ | $C_7H_7O$ | $C_{35}H_{28}O_{10}S$ |

The spectroscopical and elementary analysis data confirm the proposed structures.

EXAMPLE 36

Preparation of 4,5-bis(ethylaminocarbonyloxy)-9,10,-dihydro-9,10-dioxo-2-anthracenecarboxylic acid butyl ester The procedure of Example 8 is followed, but using 2.7 g (8 mmoles) of the product of Example 15, 2.42 g (24 mmoles) of triethylamine and about 14 ml of a 20% $COCl_2$ solution in toluene to prepare bis-chloroformate.

1.24 g (40 moles) of methylamine are used to prepare the final product.

| Elementary analysis for $C_{23}H_{22}N_2O_8$ | | |
|---|---|---|
|  | theoretical % | found % |
| C | 60,78 | 60,82 |
| H | 4,88 | 4,89 |
| N | 6,16 | 6,23 |

EXAMPLES 37–52

Following the procedure described Example 36, starting from the appropriate reagents, the following compounds are obtained:

| ES. N. | X | Y | R | Formula |
|---|---|---|---|---|
| 37 | H | $C_4H_9$ | $C_2H_5NH$ | $C_{25}H_{26}N_2O_8$ |
| 38 | H | $C_4H_9$ | $C_3H_5NH$ | $C_{27}H_{30}N_2O_8$ |
| 39 | H | $C_4H_9$ | $C_4H_9NH$ | $C_{29}H_{34}N_2O_8$ |
| 40 | H | $C_4H_9$ | $C_7H_7NH$ | $C_{35}H_{30}N_2O_8$ |
| 41 | OH | $C_4H_9$ | $CH_3NH$ | $C_{25}H_{25}N_3O_{10}$ |
| 42 | OCOR | $C_4H_9$ | $C_2H_5NH$ | $C_{28}H_{31}N_3O_{10}$ |
| 43 | OCOR | $C_2H_5OC_2H_5$ | $CH_3NH$ | $C_{23}H_{22}N_2O_9$ |
| 44 | H | $C_2H_5OC_2H_5$ | $C_2H_5NH$ | $C_{25}H_{26}N_2O_9$ |
| 45 | H | $C_2H_5OC_2H_5$ | $C_3H_7NH$ | $C_{27}H_{30}N_2O_9$ |
| 46 | H | $C_2H_5OC_2H_5$ | $C_4H_9NH$ | $C_{29}H_{34}N_2O_9$ |
| 47 | H | $C_2H_5OC_2H_5$ | $C_7H_7NH$ | $C_{35}H_{30}N_2O_9$ |
| 48 | H | $C_2H_5SC_2H_5$ | $CH_3NH$ | $C_{23}H_{22}N_2O_8S$ |
| 49 | H | $C_2H_5SC_2H_5$ | $C_2H_5NH$ | $C_{25}H_{26}N_2O_8S$ |
| 50 | H | $C_2H_5SC_2H_5$ | $C_3H_7NH$ | $C_{27}H_{30}N_2O_8S$ |
| 51 | H | $C_2H_5SC_2H_5$ | $C_4H_9NH$ | $C_{29}H_{34}N_2O_8S$ |
| 52 | H | $C_2H_5SC_2H_5$ | $C_7H_7NH$ | $C_{35}H_{30}N_2O_8S$ |

The spectroscopical and elementary analysis data confirm the proposed structures.

We claim:
1. A compound of formula (I)

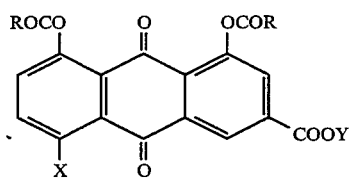

wherein:
- X is hydrogen or a OCOR group, R is a straight, branched or cyclic $C_1$–$C_{20}$ alkoxy, benzyloxy, 2-phenylethoxy group or $R^1R^2N$, wherein $R^1$ and $R^2$ are the same or different and are selected from a group consisting of hydrogen, straight, branched or alicyclic $C_1$–$C_{10}$ alkyl, phenyl, benzyl and 2-phenylethyl;
- Y is hydrogen, $C_1$–$C_{20}$ alkyl, $C_1$–$C_{16}$ alkoxyethyl or $C_1$–$C_{16}$ alkylthioethyl;

or a pharmaceutically acceptable salt thereof.

2. A compound according to claim 1, wherein Y is hydrogen or $C_1$–$C_4$ alkyl, ethoxyethyl or ethylthioethyl; R is methoxy, ethoxy, propoxy, butoxy, benzyloxy, methylamino, ethylamino, propylamino, benzylamino; and, when Y is hydrogen, a salt thereof with a pharmaceutically acceptable organic base or metal.

3. A compound according to claim 1 which is 4,5-bis(methoxycarbonyloxy)-9,10-dihydro-9,10-dioxo-2-anthracenecarboxylic acid.

4. A compound according to claim 1 which is 4,5,8-tris(methylaminocarbonyloxy)-9,10-dihydro-9,10-dioxo-2-anthracenecarboxylic acid.

5. A compound according to claim 1 which is 4,5-bis(methoxycarbonyloxy)-9,10-dihydro-9,10-dioxo-2-anthracenecarboxylic acid butyl ester.

6. A compound according to claim 1 which is 4,5-bis-(ethylaminocarbonyloxy)-9,10-dihydro-9,10-dioxo-2-anthracenecarboxylic acid butyl ester.

7. A method of treatment of a patient affected by arthritis which consists of administering to said patient a composition in unit dosage form, containing 5–500 mgs per dose, of a compound of formula (I)

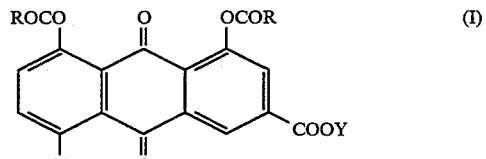

wherein:
- X is hydrogen or a OCOR group, R is a straight, branched or cyclic $C_1$–$C_{20}$ alkoxy, benzyloxy, 2-phenylethoxy group or $R^1R^2N$, wherein $R^1$ and $R^2$ are the same or different and are selected from a group consisting of hydrogen, straight, branched or alicyclic $C_1$–$C_{10}$ alkyl, phenyl, benzyl and 2-phenylethyl;
- Y is hydrogen, $C_1$–$C_{20}$ alkyl, $C_1$–$C_{16}$ alkoxyethyl or $C_1$–$C_{16}$ alkylthioethyl;

or a pharmaceutically acceptable salt thereof.

8. A pharmaceutical composition for the treatment of arthritis in unit dosage form containing 5–500 mgs per dose of a compound of formula (I)

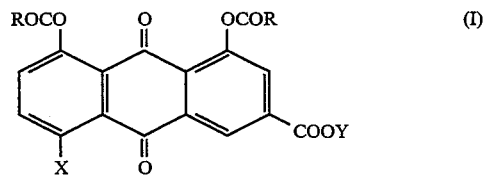

wherein:
- X is hydrogen or a OCOR group, R is a straight, branched or cyclic $C_1$–$C_{20}$ alkoxy, benzyloxy, 2-phenylethoxy group or $R^1R^2N$, wherein $R^1$ and $R^2$ are the same or different, and are selected from a group consisting of hydrogen, straight, branched or alicyclic $C_1$–$C_{10}$ alkyl, phenyl, benzyl and 2-phenylethyl;
- Y is hydrogen, $C_1$–$C_{20}$ alkyl, $C_1$–$C_{16}$ alkoxyethyl or $C_1$–$C_{16}$ alkylthioethyl;

or a pharmaceutically acceptable salt thereof.

* * * * *